(12) United States Patent
Fabry

(10) Patent No.: US 8,207,089 B1
(45) Date of Patent: Jun. 26, 2012

(54) CONCENTRATED COMPOSITIONS THAT PROVIDE DISEASE AND PEST CONTROL TO PLANTS

(75) Inventor: Carl J. Fabry, Orlando, FL (US)

(73) Assignee: Plant Food Systems, Inc., Zellwood, FL (US)

( * ) Notice: Subject to any disclaimer, the term of this patent is extended or adjusted under 35 U.S.C. 154(b) by 0 days.

(21) Appl. No.: 13/110,868

(22) Filed: May 18, 2011

Related U.S. Application Data

(63) Continuation-in-part of application No. 13/035,959, filed on Feb. 26, 2011.

(60) Provisional application No. 61/346,194, filed on May 19, 2010, provisional application No. 61/308,598, filed on Feb. 26, 2010.

(51) Int. Cl.
| | |
|---|---|
| A01N 59/04 | (2006.01) |
| A01N 37/00 | (2006.01) |
| A01N 37/44 | (2006.01) |
| A01N 65/00 | (2009.01) |
| A01N 37/10 | (2006.01) |
| A61K 31/21 | (2006.01) |
| C01D 3/08 | (2006.01) |
| B01D 11/00 | (2006.01) |
| C01B 17/62 | (2006.01) |
| C22B 26/10 | (2006.01) |

(52) U.S. Cl. ........ 504/101; 504/142; 504/147; 504/189; 504/321; 504/322; 504/324; 423/179; 423/202; 514/506

(58) Field of Classification Search ................ 504/101, 504/142, 147, 189, 321, 322, 324; 423/179, 423/202; 514/506
See application file for complete search history.

(56) References Cited

U.S. PATENT DOCUMENTS 5,076,828 A * 12/1991 Taniuchi et al. ........... 504/116.1
6,649,566 B2    11/2003 Doostdar

FOREIGN PATENT DOCUMENTS

MD     3439    * 12/2007
MD     3495    *  2/2008

* cited by examiner

*Primary Examiner* — Johann Richter
*Assistant Examiner* — Jane C Oswecki
(74) *Attorney, Agent, or Firm* — Ralph D. Chabot

(57) ABSTRACT

A composition that provides a combination of bactericidal, fungicidal, insecticidal, hormonal and nutritional activity when treating plants in an effective amount. The composition is an aqueous ammonium salicylate, potassium salicylate, and potassium acetate solution consisting essentially of:
  a first reaction product of salicylic acid and ammonium hydroxide reacted in an aqueous media with ammonium hydroxide and further reacting with a second reaction product made by combining potassium acetate and potassium hydroxide.

Urea and primary nutrients, secondary nutrients and micronutrients can be subsequently added to the composition.

11 Claims, No Drawings

CONCENTRATED COMPOSITIONS THAT PROVIDE DISEASE AND PEST CONTROL TO PLANTS

FIELD OF THE INVENTION

The present disclosure relates to concentrated agricultural plant pest spray compositions that provide, fungicidal, bactericidal, insecticidal, nutritional, and plant growth hormonal protection to plants in a single application.

BACKGROUND OF THE INVENTION

Plants are subject to a wide variety of diseases caused by assorted microorganisms (fungi, bacteria, and viruses) and damage caused by insects. Fruit bearing plants, in particular citrus trees, are subject to several destructive diseases. The bacterium *Xanthomonas axonopodis* pv. *citri* (Xac), the cause of Asiatic citrus canker (Canker), is spread by wind, rain and by mechanical means; and, Huanglongbing/Citrus Greening Disease (Greening), caused by the bacterium *Liberibacter asiaticus*, is vectored by the Asian citrus psyllid (AsCP), *Diaphorina citri* Kuwayama. Canker and Greening are particularly problematic for citrus crops as is the insect vector, psyllids. Presently, Greening is prevalent throughout all citrus producing countries in the world with no known cure. Often, governments mandate the removal and destruction of trees identified and affected with Greening.

Hundreds of thousands of acres worldwide have already been destroyed because of Canker. The Brazilian Government currently mandates that citrus trees affected with Greening be removed and burned. North American growers are not required to remove and destroy Greening trees, but are strongly urged to do so by the authorities. However, North American citrus growers could face the same destructive regulatory burdens in the future. In the US, Canker management relies heavily on the prophylactic application of copper-based compounds. These surface-only copper-based sprays have little or no effect because they are easily washed off by moisture requiring frequent reapplications throughout the growing season; thus, this approach to Canker management is inefficient, relatively expensive, and provides minimal protection at best.

Plants possess an arsenal of innate chemical defenses that are activated in response to microbial pathogens or insect pests. A number of phytohormones regulate these innate plant defenses, of which salicylic acid (SA) serves as an internal signaling molecule to systemically activate plant defenses in distal tissues through a process called systemic acquired resistance (SAR). SAR is dependent on the plant's ability to synthesize and accumulate SA that serves to trigger the downstream induction of SA dependent defense genes, including a series of pathogenesis-related (PR) genes. The expression of these PR genes can inhibit pathogen growth within the plants and reduce disease symptoms; this response is also referred to as plant basal defense and also plays an important role in genetic resistance. SAR can be triggered biologically by either subjecting the plant to a limited infection by a weak pathogen or to an avirulent pathogen (one that the plant has a genetic resistance to). However, a number of chemical compounds can also trigger SAR, such as 2,6-dichloroisonicotinic acid (INA) and benzothiadiazole (BTH), and through the exposure of plants to SA itself, or to the salts of SA described herein as the invention. The effectiveness of SAR as triggered chemically by SA, INA, and BTH has been well documented against various plant pathogens in diverse environments (Vallad and Goodman, 2005).

SA (0-hydroxybenzoic acid, CAS: 69-72-7, $C_6H_4(OH)(COOH)$ is a white powder, of very low solubility, which is commercially available in technical, USP, and crude grade, and not available in any effective, concentrated agricultural solutions for use on commercial crops. SA is only soluble in acetone, oil of turpentine, alcohol, ether, benzene and only slightly soluble in water. Some non fluid salts of SA exist as pharmaceuticals, and chemical test kits, which are not suited for agricultural usage While SA would be beneficial to plants in effective amounts, the problem has been the difficulty of maintaining SA substantially in solution for plant uptake. Foliar application of unsolubilized SA, and other improperly formulated forms can cause injury to plants.

Presently, there are no formulations of SA, registered either by the Environmental Protection Agency (EPA), or by the Association of American Plant Food Control Officials (AAPFCO), for use on crops in any form.

U.S. Pat. No. 6,649,566 issued to Doostdar discloses a stable aqueous formulation comprising salicylic acid, hydrolyzed chitosan which is a weak base, a strong inorganic base, and humic acid. The inorganic acid is used to stabilize, but not fully solubilize, the salicylic acid; and the humic acid is used to stabilize the chitosan. Doostdar implies a synergistic effect on plants by delivery of salicylic acid/chitosan combination. Although the formulation is disclosed as being a stable solution, it makes to claim to full solubility of the salicylic acid, and the Doostdar reference is silent with respect to extended solubility and shelf life and efficacy of the product. Testing confirms it is not possible to formulate a fully soluble, high analysis aqueous SA solution using only potassium hydroxide as a base for reaction which provides a long shelf life in solution.

It would be desirable to have an effective SA-based product that can be safely applied to fruit bearing plants, without phytoxicity, in a single application that will systemically stop or effectively retard damage caused by fungal and bacterial diseases and insects and provide plant growth hormonal protection to these plants. The present disclosure relates to agricultural plant spray compositions that will stop or effectively retard such damage and provide plant growth hormonal protection in one application.

SUMMARY OF THE INVENTION

The novel composition of this invention provides bactericidal, fungicidal, insecticidal, plant growth hormonal, and nutritional benefits when treating plants with an effective amount of the composition in a use diluted spray.

It is an object of the invention to provide a concentrated, stable aqueous formulation having substantially solubilized salicylic acid in salicylate form. The novel composition has a prolonged shelf life and which can be diluted with water to form a use-dilution product for foliar application to plants. The novel composition consists essentially of: aqueous solutions of a first reaction product, ammonium salicylate and excess salicylic acid, and a second reaction product, potassium acetate and excess potassium hydroxide, which are thereafter reacted together to form an aqueous, ammonium-potassium salicylate solution.

The first reaction product contains ammonium salicylate, which is formed by combining salicylic acid and ammonium hydroxide in a molar ratio of between about 1.90-2.19:1 which results in excess salicylic acid being present as a component of the first reaction product. The second reaction product contains potassium acetate, which is formed by combining potassium hydroxide and acetic acid in a molar ratio of at least about 3:1 which results in excess potassium hydroxide being present as a component of the second reaction product. Thereafter, the first reaction product and second reaction product are combined to form the novel composition. The novel composition can range from a weight ratio of from 0.01-5.0 parts first reaction product to 5.0-0.01 parts second reaction product.

Of critical note is that an excess of salicylic acid is present in the first reaction product and that an excess of potassium hydroxide is present in the second reaction product. When the first and second reaction products are combined, a reaction occurs between the excess salicylic acid and potassium hydroxide present. The novel composition is a stable, substantially solubilized salicylate solution capable of remaining in a solubilized state for a prolonged period of time.

DEFINITIONS

In the context of this disclosure, a number of terms are utilized.

The term "about" means within 20%, preferably within 10%, and more preferably within 5% of a given value or range.

The term "comprising" is intended to include embodiments encompassed by the terms "consisting essentially of" and "consisting of". Similarly, the term "consisting essentially of" is intended to include embodiments encompassed by the term "consisting of".

The term "salicylic acid" (SA), as related to this invention, means a benzene ring with a hydroxyl and carboxyl group formed as a white, crystalline material with the formula $C_6H_4(OH)COOH$; or, as a naturally occurring plant substance such as a phenolic phytohormone.

The term "salicylate", means a manufactured chemical compound salt or ester of salicylic acid, containing the monovalent, negative radical $HOC_6H_4COO$, or the group $C_7H_5O_3$.

The term "concentrated", means a solution containing at least about 4.0% salicylate.

The novel composition of this invention is a concentrated clear solution consisting essentially of the first and second reaction products described earlier. The novel composition can thereafter be appropriately diluted with water to form a use-dilution product and safely applied to plants. The solution can be delivered in effective amounts without phytotoxicity, in a single application, which will substantially retard or mitigate damage caused by fungal and bacterial diseases, hormonal imbalance, and insects.

When treated with the novel composition, the basal defenses of the plants are enhanced by supplementing SA levels in the plant. A benefit of the novel composition is that plant nutrient salts, such as ammonium and potassium, of SA can be safely applied to plants, in a completely stable, solublized form without plant injury. Thus delivery of additional SA in an effective amount to a plant serves to activate the plant's defenses by the SAR pathway.

In a preferred embodiment, other primary (nitrogen, phosphorus, potassium), secondary (calcium, magnesium, sulfur) and micro nutrients (boron, copper, iron, manganese, molybdenum, silver, zinc) can be added to the novel composition following the salicylate process; i.e. the combining of the first and second reaction products. In addition, any such fertilizer material that can be applied as a solution, as approved for use on crops, by (AAPFCO) can be added as well.

Thus, the novel composition consists essentially of the first and second reaction products discussed earlier to form a stable, substantially soluble SA containing solution which has the characteristic of having a long shelf life. Thereafter, primary, secondary and micro nutrients can be added to the novel composition since they do not enhance or detract from the primary goal of this invention, which is to provide a concentrated, substantially soluble salicylate solution formed by the blending of the first and second reaction products. Additionally, other organic and inorganic ingredients can be added after the novel composition is formed to enhance a plant's SAR.

Another aspect of the invention is a process for the application of an effective amount of the above composition to plants, such as citrus plants or other fruit bearing plants, vegetable plants, turf, ornamental plants and field crops in order to provide fungicidal, bactericidal, insecticidal protection, and hormonal and nutritional activity thereby promoting plant health and improving yields.

The novel composition can readily be augmented by cold blending the composition with an aqueous fertilizer which can include nitrogen containing compounds, such as, urea, nitrates or other ammonical compounds, effective amounts of phosphate, potassium phosphate and/or potassium compounds, and effective amounts of secondary nutrients, such as, calcium, magnesium, sulfur, and micro-nutrients, such as, boron, copper, iron, molybdenum, manganese, silver and zinc, and other plant minerals and metals.

Blending my novel composition with an aqueous fertilizer can form a stable, homogeneous and sprayable solution which not only can substantially restrict fungal and bacterial diseases and insects, but the fertilizer component can enhance plant growth, further reducing the deleterious effects of fungal and bacterial diseases and insect damage. These blended solutions are stable, clear and sprayable and have a relatively long shelf life. Also, these blended solutions are readily prepared by prescription for specific crops and specific situations and can be diluted with water if necessary when applied to plants.

The novel aqueous compositions can be cold blended with water for foliar spray application by the grower. The composition can be used in a concentrated form for metering and injection into a spray that is applied to a crop.

Working formulations of the invention can be used in any type of topical application, including both foliar and soil applications. The concentrated formulation made according to my invention can be diluted depending on the type and size of the crop to be treated. If desired, solutions of plant micronutrients or other additives, as described above, can be used to dilute the concentrated formulation.

One embodiment of the invention comprises an aqueous, ammonium-potassium salicylate solution made from combining a first reaction product consisting essentially of ammonium salicylate and excess salicylic acid, with a second reaction product consisting essentially of potassium acetate and excess potassium hydroxide. Once the aqueous, ammonium-potassium salicylate solution is formed, other components selected from the group consisting of urea, primary, secondary and micro nutrients or combinations thereof can be added and thereafter diluted for agricultural application.

DETAILED DESCRIPTION OF THE INVENTION

A first reaction product is made by combining salicylic acid with water at a weight ratio of 3.79 to 1. 1,444 pounds of water was combined with 381 pounds of pharmaceutical grade salicylic acid and thereafter, 175 pounds of a 29% solution of aqua ammonia was slowly added under vigorous agitation for about 1 hour. The molar ratio of salicylic acid to ammonium hydroxide was 1.9:1. An exothermic reaction occurred with the addition of the base but the heat of reaction was kept low by the slow addition of base to the slurry about 20 pounds of base per minute added to the slurry. A color change was observed from red at a lower pH, then amber, and then finally clear near neutral pH in order to determine completion.

The second reaction product contains potassium acetate and excess potassium hydroxide. 714 pounds of glacial acetic acid and 1,286 pounds of a 50% solution of potassium hydroxide were combined under vigorous agitation for 15 minutes.

Thereafter, the first and second reaction products are combined, and the free, excess potassium hydroxide present in the second reaction product reacts with the free excess SA present in the first reaction product to complete the formulation process; the novel composition having a crop safe pH of about 7.30.

Once the formulation process is complete, other additives can be combined with the concentrated novel composition to make a final product.

Urea can be added in various percentage weight ratios from about 1.0 to about 15.0% of the final solution as an added nutritional component and also as a buffering and wetting agent in order to facilitate faster crop uptake of the novel composition.

Characteristics of a salicylate solution include discoloration and product degradation, and reduced efficacy when exposed to light and high temperature. Therefore, production, storage and packaging is carefully managed under opaque conditions.

The following example illustrates the invention. All parts and percentages are on a weight basis.

EXAMPLE

The novel composition of this invention was formulated according to the above manufacturing process. In the following Table 1, the composition is applied and compared to other compositions in the control of a tomato disease as follows:

Tomato disease assays were performed using an aggressive field isolate of *Pseudomonas syringae* pv. *tomato* (Pst). Treatments were applied with a hand-held sprayer to the entire foliage of five week-old tomato seedlings and allowed to air dry completely. Plants treated with sterile distilled water served as the negative control. Ten individual plants were used in each treatment and arranged in a completely randomized design. Plants were inoculated 7 days after treatment application with a spray application of an approximately $2 \times 10^7$ cfu/ml suspension of Pst. Plants were allowed to air dry following inoculation before being incubated at 27° C. with 85% relative humidity for 48 hrs and then further maintained at 25° C. with 65% RH for another 4-7 days to encourage infection and symptom development. Disease severity was assessed as the total number of leaf lesions per $cm^2$ leaf area as measured with a LICOR leaf meter.

TABLE 1

Effect of the invention relative to two salicylate standards, ACTIGARD ®, and two commercial *Bacillus*-based biopesticides on the mean severity of bacterial speck (*Pseudomonas syringae* pv. tomato) on tomato plants.

| Treatment | Rate | Disease Severity[y] | Leaf Area |
|---|---|---|---|
| Invention | 6.25 ml/L | 0.43 | 17.9 |
| Salicylate | Molar equiv. to SA in Invention 1 Qt/A (66.7 mg/L) | 1.60 | 17.9 |
| Ammonium Salicylate | Molar equiv. to SA in Invention (74.9 mg/L) | 3.48 | 16.1 |
| Salicylate | 1 mM (138 mg/L) | 3.81 | 21.3 |
| Ammonium Salicylate | 1 mM (155 mg/L) | 4.30 | 17.6 |
| ACTIGARD ® | 140 mg/L | 0.92 | 21.5 |
| *Bacillus* #1 | 6.25 ml/L | 2.64 | 16.7 |
| *Bacillus* #2 | 6.25 ml/L | 3.01 | 15.1 |
| Non-treated Control | n/a | 3.56 | 20.3 |

[y]Disease severity assessed as the number of bacterial speck lesions per leaf area ($cm^2$).

ACTIGARD® is a registered trademark of Syngenta Participations AG CORPORATION SWITZERLAND. The product does not contain a salicylate. The active ingredient is acidbenzolar-S-methyl.

*Bacillus* #1 and *Bacillus* #2 are commercial SAR pesticides, SERENADE® and SONATA®, respectively which are both registered trademarks of AgraQuest Inc., Davis, Calif.

Conclusions of the test: Average disease severity for the non-treated control was 3.56 lesions/$cm^2$, while the standard ACTIGARD® treatment was less at only 0.92 lesions/$cm^2$. The two additional commercial *Bacillus*-based formulations had no effect on disease severity relative to the non-treated control. The "treatment composition made according to this invention gave a level of control that was numerically superior to the ACTIGARD® standard. A rate of salicylate that was equimolar to the invention reduced disease severity to 1.60 lesions/$cm^2$ which was higher in comparison to the treatment with the invention. The two rates of ammonium salicylate and a higher rate of salicylate were ineffective at reducing disease severity in comparison to the invention.

I claim:

1. A composition that provides a combination of bactericidal, fungicidal, insecticidal, hormonal and nutritional activity when treating plants in an effective amount comprising an aqueous ammonium salicylate and potassium salicylate solution consisting essentially of:
    a first reaction product from the combination of salicylic acid and ammonium hydroxide in a molar ratio of between about 1.90-2.19:1;
    a second reaction product from the combination of potassium acetate and potassium hydroxide in a molar ratio of about 0.33:1; and,
    where said first and second reaction products are further combined in a weight ratio of from 0.01-5.0 parts first reaction product to 5.0-0.01 parts second reaction product.

2. The composition of claim 1 additionally containing urea.

3. The composition of claim 2 additionally containing agricultural components selected from the group consisting of primary nutrients, secondary nutrients, micro-nutrients and any mixtures thereof.

4. The composition of claim 3 wherein said primary nutrients are selected from the group consisting of nitrogen containing compounds, phosphorus, potassium, and combinations thereof, said secondary nutrients selected from the group consisting of calcium, magnesium, sulfur, and any combinations thereof; and said micro-nutrients selected from the group consisting of boron, copper, iron, manganese, molybdenum, zinc and any combinations thereof.

5. The composition of claim 2 in the form of a concentrate for metering into an aqueous spray for application to plants.

6. The composition of claim 2 in the form of an aqueous premixed blend for direct foliar application to plants.

7. The composition of claim 1 further diluted with water to form a use-dilution product to treat a plant.

8. The composition of claim 3 further diluted with water to form a use-dilution product to treat a plant.

9. An aqueous composition that provides a combination of bactericidal, fungicidal, insecticidal, hormonal and nutritional activity when treating plants in an effective amount consisting essentially of ammonium salicylate, potassium salicylate, and potassium acetate.

10. The aqueous composition of claim 9 containing in addition agricultural components selected from the group consisting of primary nutrients, secondary nutrients, micronutrients and any mixtures thereof.

11. A concentrated, soluble composition made with salicylic acid consisting essentially of:
a first reaction product containing ammonium salicylate and salicylic acid; and a second reaction product containing potassium acetate and potassium hydroxide, where said first reaction product and said second reaction product are combined to further form potassium salicylate and where the weight proportion can be from 0.01 to 5.0 parts first reaction product to 5.0 to 0.01 parts second reaction product.

* * * * *